United States Patent [19]
Klemarczyk

[11] Patent Number: 5,504,252
[45] Date of Patent: Apr. 2, 1996

[54] SYNTHESIS OF CYANOACRYLATE ESTERS BY OXIDATION OF AROMATIC SELENYL CYANOPROPIONATES

[75] Inventor: Philip Klemarczyk, Collinsville, Conn.

[73] Assignee: Loctite Corporation, Hartford, Conn.

[21] Appl. No.: 435,983

[22] Filed: May 5, 1995

[51] Int. Cl.$^6$ .................................................. C07C 253/30
[52] U.S. Cl. .......................................... 558/379; 558/443
[58] Field of Search ...................................... 558/379, 443

[56] References Cited

U.S. PATENT DOCUMENTS

| | | | |
|---|---|---|---|
| 2,391,251 | 12/1945 | Long | 260/464 |
| 2,467,926 | 4/1949 | Ardis | 260/465.4 |
| 2,721,858 | 10/1955 | Joyner et al. | 260/465.4 |
| 3,254,111 | 5/1966 | Hawkins et al. | 260/465.4 |
| 3,355,482 | 11/1967 | Coover, Jr. et al. | 260/464 |
| 3,463,804 | 8/1969 | Ray et al. | 260/465 |
| 3,654,340 | 4/1972 | Banitt | 260/465.4 |
| 4,012,402 | 3/1977 | Buck | 526/298 X |
| 4,153,641 | 5/1979 | Deichert et al. | 260/827 |
| 5,140,084 | 8/1992 | Mikuni et al. | 526/279 |
| 5,140,840 | 8/1992 | Miceli | 63/12 |
| 5,359,101 | 10/1994 | Woods et al. | 556/52 |

OTHER PUBLICATIONS

Skeist, "Handbook of Adhesines", 3rd Ed,. 1990, pp. 466–467, Reinhold pub.
Schumb, et al., "Hydrogen Peroxide", 1955, p. 410; Reinhold pub.
Payne, et al., I. Org. Chem., 26, 1961, pp. 651–659.
Linn, et al., "Organic Synthesis," Coll. vol. 5, 1973, pp. 1007–1011.
Hudlicky, "Oxidations in Organic Chemistry," ACS Monograph 186, 1990, pp. 230–231.
Oakwood, et al., "Organic Synthesis", Coll. vol. 3, 1955, pp. 114–115.
Corson, et al., "Organic Synthesis", Coll. vol. 1, 1932, pp. 336–340.

*Primary Examiner*—Joseph Paul Brust
*Attorney, Agent, or Firm*—Vidas, Arrett, & Steinkraus

[57] ABSTRACT

A method of preparing an α-cyanoacrylate ester of a desired alcohol includes the steps of preparing a compound which is an α-selenoaryl-α-cyanopropionate ester of the desired alcohol, oxidizing said α-selenoaryl-α-cyanopropionate ester to the corresponding selenoxide, eliminating arylselenic acid from the selenoxide to produce said α-cyanoacrylate ester, and separating said α-cyanoacrylate ester from the selenic acid.

At temperatures of about 0° C. or higher, the elimination step occurs concurrently with the oxidizing step using a peroxide or ozone oxidizing agent. The desired cyanoacrylate ester is obtained in good yield and very high purity. The method can be used to prepare difficult to synthesize plural functional cyanoacrylate monomers and mono- cyanoacrylate monomers regardless of alcohol chain length.

24 Claims, No Drawings

SYNTHESIS OF CYANOACRYLATE ESTERS BY OXIDATION OF AROMATIC SELENYL CYANOPROPIONATES

BACKGROUND OF THE INVENTION

The most common method for the production of cyanoacrylate monomers involves the base catalyzed Knoevenagel condensation of cyanoacetate with formaldehyde, followed by acid catalyzed thermolysis of the intermediate polymer. This method is exemplified in many references, for instance U.S. Pat. Nos. 2,721,858; 3,254,111; 3,355,482; 3,654,340; 5,140,084 and 5,359,101. This method is effective and inexpensive in producing low molecular weight monomers, but as the size of the cyanoacrylate ester increases the method becomes more difficult and yields diminish substantially. Cyanoacrylate esters of monofunctional $C_8$ or higher aliphatic alcohols cannot be produced in commercially practical yields by this method.

There are several other synthetic methods known for producing cyanoacrylates including:

Diels-Alder protection/deprotection as exemplified by U.S. Pat. No. 3,463,804 and 4,012,402;

transesterification of cyanoacrylate monomers with alcohols as reported in WPI 80-82239C/46, abstracting (SU 726086 (1980));

direct esterification of cyanoacrylic acid with alcohols as reported in DE 34 15 181 (1984);

thermal decomposition of alkyl 2-cyano-3-alkoxypropionates and the 3-acyloxy analogs, reported in U.S. Pat. No. 2,467,926; and pyrolysis of the cyanohydrin acetates of pyruvic acid esters, reported in U.S. Pat. No. 2,391,251.

Monomers having a plurality of cyanoacrylate groups per molecule are particularly desirable because they can give crosslinked products on polymerization, alone or in combination with conventional monofunctional cyanoacrylate monomers. Crosslinked polymers give improved properties such as solvent resistance. The Diels-Alder protection/deprotection disclosed in U.S. Pat. No. 4,012,402 has been used to prepare various bis-cyanoacrylate monomers. However, the method is cumbersome and not suited to commercial production.

Kadykov, et. al., "Synthesis and Properties of Siloxane Cyanoacrylate Adhesives," Plast. massy, 1984, No. 10, pp.8–9, reports an alleged syntheses of "diacryl-α-cyano-β-hydroxypropyldimethylsiloxane" by reaction of one mole diepoxydimethylsiloxane and two moles α-cyanoacrylic acid in the presence of 0.03 moles tertiary amine catalyst and 0.05 mole hydroquinone monomethyl ether. The reaction is reported to be exothermic and to produce the bis-ester of the formula:

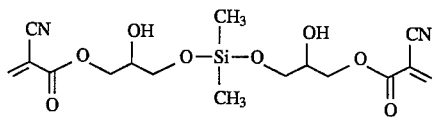

However, the reaction conditions employed make it unlikely that such a product could actually be isolated and the analytical data reported in this reference on the product which was isolated is believed to confirm that the product was not the bis-cyanoacrylate.

There therefore exists a need for further alternative methods for cyanoacrylate ester production and in particular methods which can be used for production of monomers having plural cyanoacrylate functionality in reasonable yield and with less difficulty than that of U.S. Pat. No. 4,012,402.

In Reich, et al, JACS, 97, 5434–47 (1975) and Bucheister, et al, *Organometallics*, 1, 1679–84 (1982), it is reported that certain αβ-unsaturated methyl or ethyl esters were prepared by oxidation/elimination reactions performed on corresponding methyl or ethyl α-selenoarylpropionate esters. However it has not been previously proposed or suggested to try to use such procedure to prepare α-cyanoacrylate esters, nor has it been proposed or suggested to try to prepare esters of $C_8$ or higher alcohols or plural ester compounds by preparation and oxidation/elimination of α-selenoaryl-α-cyanopropionate esters.

SUMMARY OF THE INVENTION

The present invention is directed to a novel method for preparing cyanoacrylate monomers which can be used to prepare difficult to synthesize higher molecular weight cyanoacrylate monomers and plural functional cyanoacrylate monomers as well as more conventional monofunctional cyanoacrylate monomers in high yield and by a relatively simple procedure.

The invention in one aspect is a method of preparing an α-cyanoacrylate ester of a desired alcohol, the method comprising the steps of preparing a compound which is an α-selenoaryl-α-cyanopropionate ester of said alcohol, oxidizing said α-selenoaryl-α-cyanopropionate ester to the corresponding selenoxide, eliminating arylselenic acid from said selenoxide to produce said α-cyanoacrylate ester, and separating said α-cyanoacrylate ester from said arylselenic acid.

At temperatures of about 0° C. or higher, the elimination step occurs concurrently with the oxidizing step using a peroxide or ozone oxidizing agent. The desired cyanoacrylate ester is obtained in good yield and very high purity.

DETAILED DESCRIPTION OF THE PREFERRED EMBODIMENTS

In the inventive method as described above, the α-selenoaryl-α-cyanopropionate ester is suitably prepared by treating a corresponding α-cyanopropionate ester with a base of sufficient strength to abstract an α-H atom from the cyanopropionate ester and adding an arylselenylhalide of the formula

where Ar is an aryl group and X is Cl, Br or I.

The α-cyanopropionate ester of the desired alcohol can be prepared by known means. In general any means suitable for preparing α-cyanoacetate esters can be readily modified by known methods to prepare corresponding α-cyanopropionate esters. Such methods include acid catalyzed direct esterification of cyanopropionic acid with an alcohol, optionally in the presence of 2-halopyridinium salts; base catalyzed alkylation reactions of cyanopropionic acid with alkyl halides; acid or base catalyzed transesterification reactions; nucleophilic substitution reactions where chloropropionates are treated with alkali cyanides in a direct cyanation reaction; and direct acylation reactions of alcohols with cyanopropionyl chloride.

The invention is particularly advantageous for preparing cyanoacrylate esters of $C_8$ or higher alcohols, including aliphatic and aromatic alcohols, for instance $C_8$-$C_{22}$ hydrocarbon alcohols and alkoxylated hydrocarbon alcohols such as ethoxylated nonyl phenol and similar surfactant compounds. The inventive method can also be used to prepare plural functional cyanoacrylate compounds, i.e. from cyanopropionate esters of plural hydroxy functional compounds. Such plural hydroxy functional compounds can be simple diols, triols or tetraols such as ethylene glycol, propylene glycol, 1,3-propane diol, 1,4,-butanediol, trimethylolpropane, 1,6-hexanediol, pentaerythritol, diethylene glycol, tetraethylene glycol and the like or oligomeric prepolymer compounds such as polyethylene glycol, hydroxy terminated polybutadiene, hydroxy terminated polyesters and the like.

The arylselenyl halide is suitably prepared from a diaryldiselenide such as diphenyldiselenide by addition of the molecular halogen $X_2$. Suitable Ar groups are substituted or unsubstituted phenyl groups. Suitable phenyl group substitutions include halo, alkyl, alkoxy and haloalkyl. Specific examples of substitutions include methyl, ethyl, phenyl, chloro, fluoro, trifluoromethyl, methoxy and ethoxy. Preferably X is Br.

Examples of bases of sufficient strength to abstract an α-H atom from the cyanopropionate ester include the alkali hydride bases NaH, KH, LiH, and alkylalkalides, such as n-butyllithium. Alkali hydride bases are preferred as the byproduct $H_2$ is removed continuously as a gas driving the reaction to completion. Alkali-amide bases, such as lithium diisopropyl amide, and alkoxide bases, such as sodium methoxide, are generally undesirable as they introduce additional amine or alcohol by-products which may be more difficult to completely remove during work-up of the α-selenoaryl-α-cyanopropionate ester.

Isolation and purification of the α-selenoaryl-α-cyanopropionate ester can usually be readily accomplished by dissolution in a suitable solvent such as ether (diethyl ether) and aqueous extraction of the solution followed by evaporation of the solvent. In general further purification is unnecessary but in some cases it can be beneficial. Further purification can for instance crystallization, suitably from a cooled ether solution.

The cyanoacrylate ester is formed by an oxidation/elimination reaction. The mechanism is believed to involve two steps which occur concurrently at ambient temperature but which can be separated into two stages if the oxidation is carried out at temperatures no higher than about 0° C. Reaction at temperatures above 0° C. is preferred as there is no benefit to isolating the intermediate selenoxide product of the oxidation reaction. Temperatures is excess of about 40° C. are also preferably avoided because the cyanoacrylate product may polymerize at elevated temperatures and because the reaction is highly exothermic and can become difficult to control at higher temperatures.

Suitable oxidizing agents are peroxide compounds and ozone. Hydrogen peroxide is generally preferred as it is inexpensive, effective and relatively easy to handle. Other oxidizing agents which may be particularly useful in some circumstances include m-chloroperbenzoic acid and sodium iodate.

The oxidation reaction is suitably carried out in a two phase reaction in which the α-selenoaryl-α-cyanopropionate ester is dissolved in a hydrophobic solvent such as methylene chloride, and the hydrogen peroxide is added as a solution in water, the two phases being vigorously agitated to effect reaction between the reactants in the respective phases.

At temperatures above about 0° C. elimination of the aryl selenic acid occurs spontaneously without added reactant or catalyst to yield the desired cyanoacrylate ester. The aromatic selenic acid is insoluble in common organic solvents and so is readily separated from the cyanoacrylate. In the case of the two-phase reaction described above separation of the cyanoacrylate ester is accomplished simply by separation of the organic layer.

The arylselenic acid byproduct of the reaction can be recycled by reduction to the corresponding diaryldiselenide in accordance with the known method described in the Reich et.al. reference described above, followed by conversion of the diaryldiselenide to a selenoaryl halide by reaction with chlorine, bromine or iodine.

EXAMPLES

Ethyl cyanopropionate was obtained from TCI America and was used without further purification. Diphenyl diselenide was purchased from Aldrich or Janssen and was recrystallized from ethanol prior to use. THF was distilled from sodium/benzophenone immediately before use. Sodium hydride was purchased from Aldrich as a 95% powder and was stored in a desiccator.

Reaction glassware was oven dried before use. All glassware was immersed overnight in 0.5M $H_2SO_4$, rinsed with deionized water and oven dried. All transfers of dried solvents were performed with a syringe.

Proton NMR spectra were obtained on a Varian Gemini 300 MHZ NMR spectrometer. IR analyses were done on an ATI Mattson Genesis Series FTIR.

EXAMPLE 1

PREPARATION OF 2-OCTYL CYANOACRYLATE

The method of this example may be represented by the following equation:

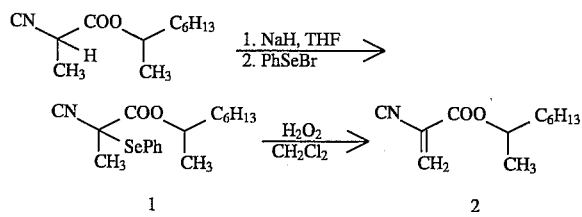

PHENYLSELENIUM BROMIDE

To a 3-neck 250 ml flask, equipped with a nitrogen inlet, magnetic stirrer, and rubber septum, was added diphenyl diselenide (20.9 g, 67 mmol) and THF (100 ml) under nitrogen. Bromine (9.8 g, 61 mmol) was added by syringe. The solution was stirred for 5 minutes.

2-Octyl Cyanopropionate phenylselenide (1)

To a 4-neck 500 ml flask, equipped with a condenser, mechanical stirrer, thermometer, and nitrogen inlet, was added sodium hydride (3.9 g, 153 mmol) and THF (250 ml) under nitrogen. 2-octyl-2-cyanopropionate (20 g, 115 mmol) was added over 10 min. and the reaction mixture was stirred for 1 hour at room temperature. A solution of phenylselenium bromide, prepared by the above method, was added by syringe. The reaction mixture was stirred for 1 hour and added to 250 ml each of ether and sat. aq. $NaHCO_3$. The organic layer was washed twice with 250 ml of $H_2O$ and once with 250 ml sat. aq. NaCl. The organic layer was separated, dried (MgSO$_4$) and filtered. Solvent was removed under reduced pressure. Yield=43.2 g (quant.); NMR δ (CDCl$_3$) 7.75 (d, 2H), 7.40 (m, 3H), 4.85 (m, 2H), 1.80 (s, 3H), 0.8–1.70 (m, 16H); IR (neat) 2333, 1734, 1251 cm$^{-1}$.

2-Octyl Cyanoacrylate (2)

To a 500 ml flask, equipped with a condenser, mechanical stirrer, thermometer, and addition funnel, was added the crude 2-octyl propionate phenylselenide (43.2 g, 115 mmol) and methylene chloride (300 ml). Hydrogen peroxide, 30% (47 g, 418 mmol) was dissolved in water (30 ml) and added to the reaction flask over 15 minutes. The reaction temperature was kept at 20°–30° C. with an ice bath. After the addition was complete, the reaction mixture was stirred for 1 hour at room temperature. The organic layer was separated and washed once with 100 ml of H$_2$O. The organic layer was separated, dried (anhydr. silicic acid), and filtered. Solvent was removed under reduced pressure. The crude product was distilled under vacuum. Yield=14.4 g (60%), B.P.=95° C./1.0 mm Hg; NMR δ (CDCl$_3$) 7.05 (s, 1H), 6.60 (s, 1H), 5.05 (m, 2H), 0.8–1.7 (m, 16H); IR (neat) 2236, 1732, 1649, 1287 cm$^{-1}$; strong acid ≤1 ppm.

EXAMPLE 2

Preparation of 1,4 Butanediol dicyanoacrylate (BDDCA)

1,4 Butanediol dicyanopropionate

To a 1000 ml 3-neck flask equipped with a Dean-Stark trap, condenser, thermometer, and nitrogen inlet, was added ethyl-2-cyanopropionate (50.8 g, 400 mmol), 1,4 butanediol (15.8 g, 175 mmol), p-toluenesulfonic acid (3 g, 16 mmol), and toluene (500 ml) under nitrogen. The solution was heated to reflux with stirring. Solvent was removed through the Dean-Stark trap and replaced with an equal volume of fresh toluene. After refluxing for 8 hours, and removing 500 ml of solvent, the solution was cooled to room temperature. The solution was washed twice with 300 ml of sat. aq. NaHCO$_3$, twice with 300 ml of H$_2$O, and once with 300 ml of sat. aq. NaCl. The organic layer was separated, dried (MgSO$_4$), and filtered. Solvent was removed under reduced pressure. The crude product was purified by vacuum distillation. Yield=22.3 g (51%), B.P.=172° C. (0.6 mm/Hg); NMR δ(CDCl$_3$) 4.25 (br t, 4H), 3.60 (q, 2H), 1.80 (br t, 4H), 1.60 (d, 6H); IR (neat) 2252, 1745 cm$^{-1}$.

PHENYLSELENIUM BROMIDE

To a 3-neck 250 ml flask, equipped with a nitrogen inlet, magnetic stirrer, and rubber septum, was added diphenyl diselenide (17.2 g, 55 mmol) and THF (100 ml) under nitrogen. Bromine (7.2 g, 45 mmol) was added by syringe. The solution was stirred for 5 min.

1,4 Butanediol dicyanopropionate bis-phenylselenide

To a 500 ml 4-neck flask, equipped with a condenser, mechanical stirrer, thermometer, rubber septum, and nitrogen inlet was added sodium hydride (2.7 g, 105 mmol) and anhydrous dimethyl formamide (200 ml) under nitrogen. Butanediol dicyanopropionate (10 g, 40 mmol) was added over 10 min. at room temperature, and the reaction mixture was stirred for 2 hours. The previously prepared phenylselenium bromide solution was added by syringe and the reaction mixture was stirred for 2.5 hours. The reaction mixture was added to 250 ml each of ether and sat. aq. NaHCO$_3$. The organic layer was washed twice with 250 ml of H$_2$O and once with 250 ml of sat. aq. NaCl. The organic layer was separated, dried (MgSO$_4$), and filtered. Solvent was removed under reduced pressure. Crude Yield=23.4 g (quant.). To the crude product was added 10 ml of ether and the mixture was cooled in an ice bath. The bis-phenylselenide precipitated, was filtered, and washed with 5 ml of cold ether. Yield =6.5 g (29%), M.P.=113° C.; NMR δ (CDCl$_3$) 7.75 (d, 4H), 7.40 (m, 6H), 3.95 (m, 4H), 1.85 (s, 6H), 1.40 (br s, 4H); IR (KBr) 2231, 1730, 1234 cm$^{-1}$.

1,4 Butanediol dicyanoacrylate (BDDCA)

To a 250 ml flask, equipped with a condenser, mechanical stirrer, thermometer, and addition funnel, was added bis-phenyselenide (6.5 g, 12 mmol) and methylene chloride (50 ml). Hydrogen peroxide, 30% (11.6 g, 102 mmol) was dissolved in water (8 ml) and added slowly to the reaction flask over 10 min. The temperature was maintained at 20°–30° C. with an ice bath. After the addition was complete, the reaction mixture was stirred for 2 hours at room temperature. The organic layer was separated and washed with 50 ml of water The organic layer was separated, dried (anhydr. silicic acid) and filtered into a flask containing 0.015 g of methanesulfonic acid. The solution was condensed under reduced pressure. Because of its reactivity, BDDCA was kept as a solution until just prior to use. Solvent was evaporated under vacuum in a desiccator from a plastic beaker, which had been immersed overnight in 0.5M H$_2$SO$_4$, washed with deionized water and dried. The solid BDDCA is extremely reactive and was used immediately after evaporation of solvent, because it polymerized within a few minutes in the solid state. M.P.=80° C.; NMR δ (CDCl$_3$) 7.10 δ(s, 2H), 6.65 (s, 2H), 4.35 (br t, 4H), 1.90 (br t, 4H); IR (KBr) 3.32 2237, 1729, 1615 cm$^{-1}$. TGA analysis showed that BDDCA homopolymer decomposed at about 65 ° C. higher than ethyl cyanoacrylate homopolymer. Polymerized mixtures of BDDCA at levels of 1, 5, 10 and 20 parts per hundred in ethyl cyanoacrylate, did not show any enhancement of thermal stability over the ethyl cyanoacrylate homopolymer but did give significant solvent swelling resistance on immersion in methylene chloride overnight.

EXAMPLES 3–7

When example 1 is repeated except that equivalent amounts of phenyl 2-cyanopropionate, 4-ethylphenyl cyanopropionate, n-octyl cyanopropionate, 4-nonylphenyl 2-cyanopropionate and stearyl 2-cyanopropionate are substituted in separate respective experimental runs for the starting 2-octyl 2-cyanopropionate used in example 1 and appropriate equivalent weight adjustments are made throughout the procedure, phenyl cyanoacrylate, 4-ethylphenyl cyanoacrylate, n-octyl cyanoacrylate, 4-nonylphenyl cyanoacrylate and stearyl cyanoacrylate, respectively will be obtained in reasonable purity at the end of the procedure.

EXAMPLES 8–12

When example 2 is repeated except that an equivalent amount of the 2-cyanopropionate esters of the following polyols are substituted in separate experimental runs for the starting 1,4-butane diol dicyanopropionate used in example 2 and appropriate equivalent weight adjustments are made throughout the procedures, the corresponding plural cyanoacrylate will be obtained in at the end of the procedure:

bis-hydroxy terminated polyethylene glycol 400;

bis-hydroxy terminated polyethylene glycol 1000;

bis-hydroxy terminated polybutadiene;

bis-hydroxy terminated mixed ortho and para phthalate/ diethylene glycol polyester;

tris-hydroxy terminated adipate/1,4-butane diol-glycerine polyester (1 eq glycerol per molecule.

What is claimed is:

1. A method of preparing an α-cyanoacrylate ester of a preselected alcohol, the method comprising the steps of preparing a compound which is an α-selenoaryl-α-cyano propionate ester of said alcohol, oxidizing said α-selenoaryl-α-cyanopropionate ester to the corresponding selenoxide, eliminating arylselenic acid from said selenoxide to produce said α-cyanoacrylate ester, and separating said α-cyanoacrylate ester from said arylselenic acid.

2. A method as in claim 1 wherein said separation step comprises an extraction of said α-cyanoacrylate ester into an organic solvent.

3. A method as in claim 1 wherein said preselected alcohol is a $C_8$ or higher mono or plural hydroxy functional compound.

4. A method as in claim 1 wherein said preselected alcohol is a compound having more than one hydroxy group per molecule and said α-selenoaryl-α-cyanopropionate ester is the ester corresponding to the esterification product of each said hydroxy group with α-cyanopropionic acid.

5. A method as in claim 4 wherein said preselected alcohol is a diol.

6. A method as in claim 1 wherein said α-selenoaryl-α-cyanopropionate ester is prepared by reaction of a selenoaryl halide of the formula:

Ar—Se—X where Ar is an aryl group and X is Cl, Br or I, with the α-cyanopropionate ester of said alcohol.

7. A method as in claim 6 wherein X is Cl.

8. A method as in claim 6 wherein X is Br.

9. A method as in claim 1 wherein, after said separation step, said arylselenic acid is recycled by reduction to the corresponding diaryldiselenide and conversion of said diaryldiselenide to a selenoaryl halide by reaction with chlorine, bromine or iodine.

10. A method as in claim 1 wherein said oxidizing step is effected by reaction of said α-selenoaryl-α-cyanopropionate ester with an oxidizing agent selected from the group consisting of peroxide compounds and ozone.

11. A method as in claim 10 wherein said oxidizing agent is hydrogen peroxide and said reaction is effected in an agitated two phase reaction mixture, one phase being an aqueous phase containing said hydrogen peroxide and the other phase being a non-aqueous phase containing said α-selenoaryl-α-cyanopropionate ester.

12. A method of preparing an α-cyanoacrylate ester of a preselected alcohol, the method comprising the steps of preparing a compound which is an α-selenoaryl-α-cyanopropionate ester of said alcohol, treating said α-selenoaryl-α-cyanopropionate ester with an oxidizing agent selected from the group consisting of peroxide compounds and ozone, and subjecting the reaction mixture at the time of or subsequent to said treatment to a temperature in excess of 0° C. to produce said α-cyanoacrylate ester and arylselenic acid, and then separating said α-cyanoacrylate ester from the arylselenic acid.

13. A method as in claim 12 wherein said separation step comprises an extraction of said α-cyanoacrylate ester into an organic solvent.

14. A method as in claim 12 wherein said preselected alcohol is a $C_8$ or higher mono or plural hydroxy functional compound.

15. A method as in claim 12 wherein said preselected alcohol is a compound having more than one hydroxy group per molecule and said α-selenoaryl-α-cyanopropionate ester is the ester corresponding to the esterification product of each said hydroxy group with α-cyanopropionic acid.

16. A method as in claim 15 wherein said preselected alcohol is a diol.

17. A method as in claim 12 wherein said α-selenoaryl-α-cyanopropionate ester is prepared by reaction of a selenoaryl halide of the formula:

Ar—Se—X where Ar is an aryl group and X is Cl, Br or I, with the α-cyanopropionate ester of said alcohol.

18. A method as in claim 17 wherein X is Cl.

19. A method as in claim 17 wherein X is Br.

20. A method as in claim 17 wherein Ar is phenyl which is unsubstituted or substituted by one or more halo, alkyl, haloalkyl or alkoxide groups.

21. A method as in claim 12 wherein, after said separation step, said arylselenic acid is recycled by reduction to the corresponding diaryldiselenide and conversion of said diaryldiselenide to a selenoaryl halide by reaction with chlorine, bromine or iodine.

22. A method as in claim 12 wherein said oxidizing agent is hydrogen peroxide and said reaction is effected in an agitated two phase reaction mixture, one phase being an aqueous phase containing said hydrogen peroxide and the other phase being a non-aqueous phase containing said α-selenoaryl-α-cyanopropionate ester.

23. A method as in claim 6 wherein Ar is phenyl which is unsubstituted or substituted with one or more halo, alkyl, haloalkyl or alkoxide groups.

24. A method of preparing an α-cyanoacrylate ester of a preselected alcohol, the method comprising the steps of preparing a compound which is an α-selenoaryl-α-cyanopropionate ester of said alcohol, the aryl group of said α-selenoaryl-α-cyanopropionate ester being phenyl which is unsubstituted or substituted with one or more halo, alkyl, haloalkyl or alkoxide groups, treating said α-selenoaryl-α-cyano propionate ester with an oxidizing agent selected from the group consisting of peroxide compounds and ozone, and subjecting the reaction mixture at the time of or subsequent to said treatment to a temperature in excess of 0° C. to produce said α-cyanoacrylate ester and arylselenic acid, and then separating said α-cyanoacrylate ester from the arylselenic acid, said separation step comprising an extraction of said α-cyanoacrylate ester into an organic solvent.

* * * * *